(12) United States Patent
Kato et al.

(10) Patent No.: US 10,918,845 B2
(45) Date of Patent: Feb. 16, 2021

(54) TRANSDERMAL ADMINISTRATION DEVICE

(71) Applicant: TOPPAN PRINTING CO., LTD., Taito-ku (JP)

(72) Inventors: Hiroyuki Kato, Taito-ku (JP); Ichiro Takase, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 124 days.

(21) Appl. No.: 15/647,540

(22) Filed: Jul. 12, 2017

(65) Prior Publication Data

US 2017/0304603 A1 Oct. 26, 2017

Related U.S. Application Data

(63) Continuation of application No. PCT/JP2016/050339, filed on Jan. 7, 2016.

(30) Foreign Application Priority Data

Jan. 13, 2015 (JP) .............................. JP2015-004381

(51) Int. Cl.
*A61M 37/00* (2006.01)
*A61B 17/20* (2006.01)
*A61M 5/142* (2006.01)

(52) U.S. Cl.
CPC ....... *A61M 37/0015* (2013.01); *A61B 17/205* (2013.01); *A61M 5/14248* (2013.01);
(Continued)

(58) Field of Classification Search
CPC .......... A61M 5/14248; A61M 37/0015; A61M 2037/0023; A61M 2037/0046; A61B 17/205
See application file for complete search history.

(56) References Cited

U.S. PATENT DOCUMENTS 7,789,733 B2 9/2010 Sugimura et al.
8,292,696 B2 10/2012 Sugimura et al.
(Continued)

FOREIGN PATENT DOCUMENTS

JP 2007-537783 A 12/2007
JP 2008-512199 A 4/2008
(Continued)

OTHER PUBLICATIONS

International Search Report dated Mar. 22, 2016 in PCT/JP2016/050339, filed Jan. 7, 2016.

*Primary Examiner* — Laura A Bouchelle
*Assistant Examiner* — Anh Bui
(74) *Attorney, Agent, or Firm* — Oblon, McClelland, Maier & Neustadt, L.L.P.

(57) ABSTRACT

A transdermal administration device including a first administration member including a first substrate and a first projection protruding from a first administration surface of the first substrate, and a second administration member including a second substrate and a second projection protruding from a second administration surface of the second substrate. The first substrate has an aperture, and the second substrate is positioned within the aperture when viewed in a direction perpendicular to the second administration surface.

20 Claims, 5 Drawing Sheets

(52) U.S. Cl.
CPC ............... *A61M 2037/0023* (2013.01); *A61M 2037/0046* (2013.01); *A61M 2037/0053* (2013.01)

(56) References Cited

U.S. PATENT DOCUMENTS

| | | | |
|---|---|---|---|
| 8,377,364 B2 | 2/2013 | Shiomitsu et al. | |
| 8,876,575 B2 | 11/2014 | Sugimura et al. | |
| 9,238,384 B2 | 1/2016 | Shiomitsu et al. | |
| 2005/0271684 A1* | 12/2005 | Trautman | A61K 9/0021 424/204.1 |
| 2006/0051403 A1* | 3/2006 | Matriano | A61K 9/0021 424/448 |
| 2008/0200883 A1 | 8/2008 | Tomono | |
| 2008/0208134 A1 | 8/2008 | Tomono | |
| 2009/0131887 A1 | 5/2009 | Shiomitsu et al. | |
| 2009/0292254 A1 | 11/2009 | Tomono | |
| 2009/0292255 A1 | 11/2009 | Tomono | |
| 2015/0246214 A1* | 9/2015 | Simmers | A61M 37/0015 604/506 |
| 2015/0374967 A1* | 12/2015 | Fudoji | A61M 37/0015 604/173 |

FOREIGN PATENT DOCUMENTS

| | | |
|---|---|---|
| WO | WO 2008/004597 A1 | 1/2008 |
| WO | WO 2008/013282 A1 | 1/2008 |
| WO | WO 2008/020632 A1 | 2/2008 |
| WO | WO 2014/126101 A1 | 8/2014 |

* cited by examiner

TRANSDERMAL ADMINISTRATION DEVICE

CROSS-REFERENCE TO RELATED APPLICATIONS

The present application is a continuation of International Application No. PCT/JP2016/050339, filed Jan. 7, 2016, which is based upon and claims the benefits of priority to Japanese Application No. 2015-004381, filed Jan. 13, 2015. The entire contents of these applications are incorporated herein by reference.

BACKGROUND OF THE INVENTION

Field of the Invention

The present invention relates to transdermal administration devices used for drug administration.

Discussion of the Background

Use of transdermal administration devices having an administration part such as a microneedle is known as a method for administering drugs into the body via the skin. The microneedle includes a plurality of needle-shaped projections formed on the surface of a substrate. The transdermal administration device includes the microneedle and an adhesive sheet for affixing the microneedle to the skin. In the administration method using a transdermal administration device, the adhesive sheet is affixed to the skin, and the microneedle substrate is pressed against the skin so that the projections puncture the skin to form holes, through which a drug is delivered into the skin.

This microneedle is produced by filling a material for forming microneedle into a mold having an inverted shape of the projections and recesses of the microneedle (for example, see PTL 1 to 3). A drug may be applied on the surface of the projections and introduced into the skin when the projections puncture the skin, or alternatively, a drug may be contained in the forming material of the projections and introduced into the skin as the projections dissolve after being pierced into the skin.

PTL 1: WO 2008/013282
PTL 2: WO 2008/004597
PTL 3: WO 2008/020632

SUMMARY OF THE INVENTION

According to an aspect of the present invention, a transdermal administration device includes a first administration member including a first substrate and a first projection protruding from a first administration surface of the first substrate, and a second administration member including a second substrate and a second projection protruding from a second administration surface of the second substrate. The first substrate has an aperture, and the second substrate is positioned within the aperture when viewed in a direction perpendicular to the second administration surface.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
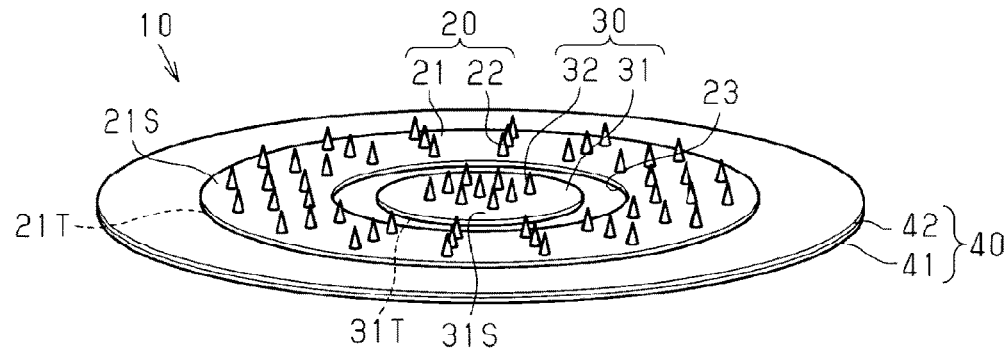
FIG. 1 is a perspective view which illustrates a perspective structure of a transdermal administration device of a first embodiment.

The embodiments will now be described with reference to the accompanying drawings, wherein like reference numerals designate corresponding or identical elements throughout the various drawings.

First Embodiment

Figure 2:
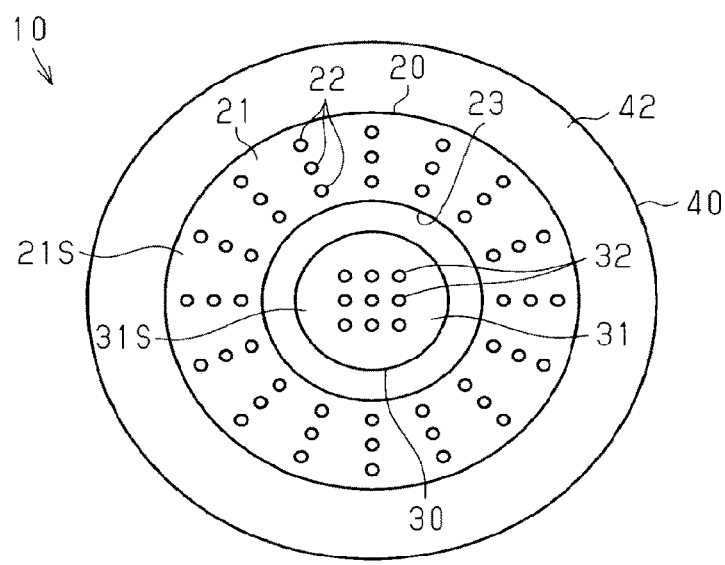
FIG. 2 is a plan view which illustrates a plan structure of the transdermal administration device of the first embodiment.

With reference to FIGS. 1 to 7, a first embodiment of a transdermal administration device will be described.
<Configuration of Transdermal Administration Device>
With reference to FIGS. 1 and 2, an overall configuration of a transdermal administration device will be described.

As shown in FIG. 1, a transdermal administration device 10 includes an outer needle 20 which is an example of a first administration member, an inner needle 30 which is an example of a second administration member, and an adhesive sheet 40.

The outer needle 20 includes a plate-shaped outer substrate 21, and outer projections 22 protruding from the outer substrate 21. The outer substrate 21 has a first administration surface 21S on which the outer projections 22 are formed, and a first non-administration surface 21T which is a surface opposite from the first administration surface 21S. The first surface 21S supports the bases of the outer projections 22. The outer substrate 21 has a circular annular shape as viewed in a first direction which is perpendicular to the first administration surface 21S, and a circular aperture 23 defined by an inner peripheral edge of the outer substrate 21.

The inner needle 30 includes a plate-shaped inner substrate 31, and inner projections 32 protruding from the inner substrate 31. The inner substrate 31 has a second administration surface 31S on which the inner projections 32 are formed, and a second non-administration surface 31T which is a surface opposite from the second administration surface 31S. The second administration surface 31S supports the bases of the inner projections 32. When viewed in a second direction which is perpendicular to the second administration surface 31S, the inner substrate 31 has a circular shape and is disposed in a space surrounded by the outer substrate 21, that is, inside the aperture 23.

In the present embodiment, the first direction and the second direction are the same direction. In other words, the direction in which the first administration surface 21S of the outer substrate 21 is oriented and the direction in which the second administration surface 31S of the inner substrate 31 is oriented are the same direction, and the direction in which the first non-administration surface 21T of the outer substrate 21 and the direction in which the second non-administration surface 31T of the inner substrate 31 are the same direction. Further, the extending direction of the outer projection 22 and the extending direction of the inner projection 32 are the same direction.

The adhesive sheet 40 includes a base sheet 41 and an adhesive layer 42 which covers one of two surfaces of the base sheet 41. The adhesive layer 42 is adhered to the first non-administration surface 21T of the outer substrate 21 and the second non-administration surface 31T of the inner substrate 31.

The outer projection 22 may be a pyramid or cone shape. Further, the outer projection 22 may be a shape which does not have a pointed tip, for example, a prism or cylinder shape. The outer projection 22 may be a shape of a combination of two or more three-dimensional shapes, for example, a cone stacked on a cylinder. The inner projection 32 may also be a pyramid or cone shape, a shape which does not have a pointed tip, or a shape of a combination of two or more three-dimensional shapes. The shape of the outer projection 22 and the shape of the inner projection 32 may be the same or different from each other. In other words, the outer projection 22 and the inner projection 32 may be any shape that can pierce the skin. Moreover, the outer projection 22 and the inner projection 32 may have a narrow portion or a shoulder formed on the side wall.

The number of the outer projections 22 and the inner projection 32 is not specifically limited. One or more outer projections 22 and one or more inner projection 32 may be provided. When the outer needle 20 includes a plurality of outer projections 22, the plurality of outer projection 22 may be arranged regularly or irregularly on the first administration surface 21S of the outer substrate 21. Similarly, when the inner needle 30 includes a plurality of inner projections 32, the plurality of inner projections 32 may be arranged regularly or irregularly on the second administration surface 31S of the inner substrate 31. The arrangement pattern of the outer projection 22 and the arrangement pattern of the inner projection 32 may be the same or different from each other.

As shown in FIG. 2, the outer shape of the adhesive sheet 40 is larger than that of the outer substrate 21 as viewed in a direction perpendicular to the first administration surface 21S of the outer substrate 21 and a direction perpendicular to the second administration surface 31S of the inner substrate 31, that is, the first direction and the second direction.

In other words, the adhesive sheet 40 extends outward from the outer substrate 21 when viewed in the perpendicular direction. The outer shape of the adhesive sheet 40 is not specifically limited, and the adhesive sheet 40 has, for example, a circular shape when viewed in the perpendicular direction.

The inner substrate 31 has a circular shape smaller than the shape formed by the inner peripheral edge of the outer substrate 21 when viewed in the perpendicular direction. A gap is formed between the outer peripheral edge of the inner substrate 31 and the inner peripheral edge of the outer substrate 21 so as to surround the entire circumference of the inner substrate 31 as viewed in the perpendicular direction, and the adhesive sheet 40 is exposed through the gap. More specifically, the adhesive layer 42 of the adhesive sheet 40 is exposed between the outer peripheral edge of the inner substrate 31 and the inner peripheral edge of the outer substrate 21 and outside the outer substrate 21 as viewed in the perpendicular direction.

In the above configuration, the outer substrate 21 is an example of a first substrate, and the outer projection 22 is an example of a first projection. Further, the inner substrate 31 is an example of a second substrate, and the inner projection 32 is an example of a second projection.

<Configuration of Administration Member>

Figure 3:
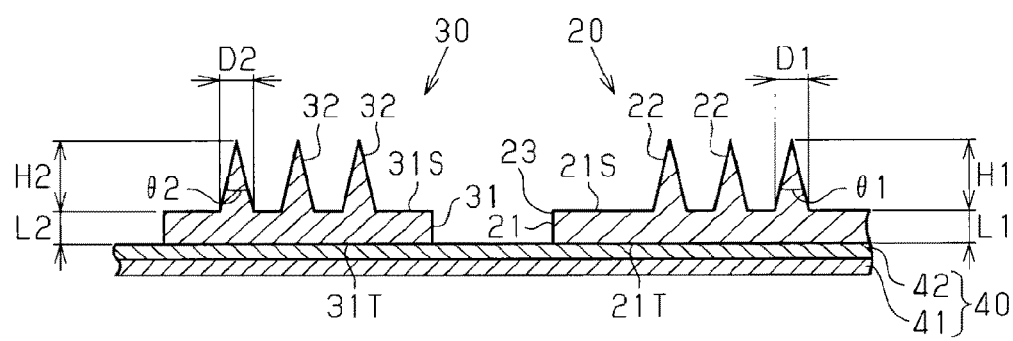
FIG. 3 is a cross-sectional view which illustrates a partial cross-sectional structure of the transdermal administration device of the first embodiment.

With reference to FIG. 3, the detailed configuration of the outer needle 20 and the inner needle 30 will be described.

As shown in FIG. 3, the length H1 of the outer projection 22 is a length from the first administration surface 21S of the outer substrate 21 to the tip of the outer projection 22 in the first direction. Further, the length H2 of the inner projection 32 is a length from the second administration surface 31S of the inner substrate 31 to the tip of the inner projection 32 in the second direction. Preferably, the length H1 of the outer projection 22 and the length H2 of the inner projection 32 are each in the range of 10 μm or more and 1000 μm or less. The length H1 of the outer projection 22 and the length H2 of the inner projection 32 may be the same or different from each other.

The length H1 of the outer projection 22 and the length H2 of the inner projection 32 are each determined within the above range depending on the depth required for the holes to be punctured by the projections 22 and 32. When the puncture target is the human skin and the depth of the hole is designed to be in the stratum corneum, the lengths H1 and H2 are preferably in the range of 10 μm or more and 300 μm or less, more preferably in the range of 30 μm or more and 200 μm or less. When the depth of the hole is designed to penetrate through the stratum corneum and not to reach the nerve, the lengths H1 and H2 are preferably in the range of 200 μm or more and 700 μm or less, more preferably in the range of 200 μm or more and 500 μm or less, and further more preferably in the range of 200 μm or more and 300 μm or less. When the depth of the hole is designed to reach the dermis, the lengths H1 and H2 are preferably in the range of 200 μm or more and 500 μm or less. When the depth of the hole is designed to reach the epidermis, the lengths H1 and H2 are preferably in the range of 200 μm or more and 300 μm or less.

The outer projection 22 has a width D1 which is a maximum length of the outer projection 22 in a direction parallel with the first administration surface 21S of the outer substrate 21. Further, the inner projection 32 has a width D2 which is a maximum length of the inner projection 32 in a direction parallel with the second administration surface 31S of the inner substrate 31. For example, when the outer projection 22 has a regular quadrangular pyramid or regular quadrangular prism shape, the width D1 of the outer projection 22 is a diagonal length of a square defined by the bottom of the outer projection 22 on the first administration surface 21S of the outer substrate 21. Further, when the outer projection 22 has a cone or cylinder shape, the width D1 of the outer projection 22 is a diameter of a circle defined by the bottom of the outer projection 22.

Preferably, the width D1 of the outer projection 22 and the width D2 of the inner projection 32 are each in the range of 1 µm or more and 300 µm or less. The width D1 of the outer projection 22 and the width D2 of the inner projection 32 may be the same or different from each other.

An aspect ratio A1 which is a ratio of the length H1 to the width D1 of the outer projection 22 (A1=H1/D1) is preferably in the range of 1 or more and 10 or less. Further, an aspect ratio A2 which is a ratio of the length H2 to the width D2 of the inner projection 32 (A2=H2/D2) is preferably in the range of 1 or more and 10 or less. The aspect ratio A1 of the outer projection 22 and the aspect ratio A2 of the inner projection 32 may be the same or different from each other.

When the tip of the outer projection 22 is formed in a pointed shape and the hole is created by the outer projection 22 to penetrate the stratum corneum, the tip angle θ1 of the outer projection 22 is preferably in a range of 5° or more and 30° or less, more preferably in a range of 10° or more and 20° or less. The tip angle θ1 is a maximum angle made by the tip of the outer projection 22 in a cross section perpendicular to the first administration surface 21S of the outer substrate 21. For example, when the outer projection 22 has a regular quadrangular pyramid shape, the tip angle θ1 of the outer projection 22 is an apex angle of a triangle having a diagonal line of a square defined by the bottom of the outer projection 22 as a base and the apex of the regular quadrangular pyramid as an apex.

When the tip of the inner projection 32 is formed in a pointed shape and the hole is formed by the inner projection 32 to penetrate the stratum corneum, the tip angle θ2 of the inner projection 32 is preferably in a range of 5° or more and 30° or less, more preferably in a range of 10° or more and 20° or less. The tip angle θ2 is a maximum angle made by the tip of the inner projection 32 in a cross section perpendicular to the second administration surface 31S of the inner substrate 31.

The tip angle θ1 of the outer projection 22 and the tip angle θ2 of the inner projection 32 may be the same or different from each other.

The width D1, the aspect ratio A1, and the tip angle θ1 of the outer projection 22 are determined depending on the volume or the like required for the holes to be formed by the outer projection 22. Further, the width D2, the aspect ratio A2, and the tip angle θ2 of the inner projection 32 are determined depending on the volume or the like required for the holes to be formed by the inner projection 32. When the lengths H1, H2, the widths D1, D2, the aspect ratios A1, A2, and the tip angles θ1, θ2 are within the above ranges, the shapes of the projections 22 and 32 are in the forms suitable for forming the holes into the skin.

The outer substrate 21 has a thickness L1 which is a length from the first administration surface 21S to the first non-administration surface 21T in a cross section perpendicular to the first administration surface 21S of the outer substrate 21, and the inner substrate 31 has a thickness L2 which is a length from the second administration surface 31S to the second non-administration surface 31T in a cross section perpendicular to the second administration surface 31S of the inner substrate 31. The thickness L1 of the outer substrate 21 and the thickness L2 of the inner substrate 31 are not specifically limited, and the thickness L1 of the outer substrate 21 and the thickness L2 of the inner substrate 31 may be the same or different from each other.

Each of the outer needle 20 and the inner needle 30 are made of a water soluble material or a thermoplastic resin. Each of the outer needle 20 and the inner needle 30 are preferably made of a biocompatible material. The outer needle 20 and the inner needle 30 may be made of the same material or different materials.

The water soluble material may be a water soluble polymer or polysaccharide. Examples of water soluble polymer include carboxymethyl cellulose (CMC), methylcellulose (MC), hydroxylpropyl cellulose (HPC), hydroxypropyl methylcellulose (HPMC), polyvinyl alcohol (PVA), polyacrylic acid polymer, polyacrylic amide (PAM), polyethylene oxide (PEO), pullulan, alginate, pectin, chitosan, chitosan succinamide, and oligochitosan. Among the above materials, chitosan, chitosan succinamide, carboxymethyl cellulose (CMC), hydroxylpropyl cellulose (HPC), hydroxypropyl methylcellulose (HPMC) are advantageously used since they have high biological safety. Further, the disaccharide may be trehalose or maltose. However, the water soluble material forming each of the outer needle 20 and the inner needle 30 is not limited to the above materials.

Examples of thermoplastic resin material include polylactic acid, cycloolefin copolymer, polyethylene, polypropylene, polycarbonate, polyglycolic acid, and the like. However, the thermoplastic resin material forming each of the outer needle 20 and the inner needle 30 is not limited to the above materials.

The outer projection 22 and the inner projection 32 each hold a drug. When the projections 22 and 32 are made of a water soluble material, a drug is contained in the projections 22 and 32. When the projections 22 and 32 are made of a thermoplastic resin, a drug is applied on the projections 22 and 32. Further, the water soluble polymer that constitutes the projections 22 and 32 may serve as a drug.

Any kind of drug may be used as long as it works when administered into the skin. Examples of a drug include various types of proteins, pharmacologically active agents, or cosmetic compositions, which are appropriately selected depending on the purpose. The drug held by the outer projection 22 and the drug held by the inner projection 32 may be the same or different from each other regardless of the drug holding form.

Examples of a pharmacologically active agent include vaccines such as influenza vaccine, pain relievers for cancer patients, insulin, biologics, gene therapy agents, injections, oral agents, skin application preparations and the like. In transdermal administration using a microneedle such as the needles 20 and 30, a drug is administered into a hole created in the skin. Therefore, transdermal administration using a microneedle can be applied to not only administration of the pharmacologically active agents used in the conventional transdermal administration, but also administration of pharmacologically active agents that require hypodermic injection. In particular, transdermal administration using a microneedle is suitable for administration of an injection medication such as vaccines for children since it does not cause pain to a patient in administration. Further, transdermal administration using a microneedle is suitable for administration of an oral medication for children who have difficulty in swallowing an oral medication since it does not require a patient to swallow a drug during administration.

Cosmetic compositions are compositions for use as cosmetics or beauty products. Examples of a cosmetic composition include humectants, colorants, fragrance, and physiologically active agents exhibiting cosmetic effects such as improvement effect on wrinkles, acne, stretch marks or the like, and improvement effect on hair loss or the like. When an aromatic material is used as a cosmetic composition, a fragrance can be imparted to the needles 20 and 30. Accordingly, the needles 20 and 30 suitable for use as a beauty product can be obtained.

Materials of the adhesive sheet 40 are not specifically limited, but the base sheet 41 may be formed of a resin film made of polyolefin resin such as polyethylene and polypropylene, polyester resin such as nylon and polyethylene terephthalate, or polyvinyl chloride, polyvinylidene chloride, polyurethane, polyvinyl alcohol or the like. Further, the adhesive layer 42 may be formed of, for example, a silicone, urethane, epoxy, or acrylic adhesive.

The outer projection 22 included in the outer needle 20 and the inner projection 32 included in the inner needle 30 have different administration functions which are exhibited in drug administration.

For example, the administration function of the outer projection 22 and the administration function of the inner projection 32 are different in the kind of drug administered during puncture by the projection. In this case, the kinds of drugs held by the outer projection 22 and the drug held by the inner projection 32 are different from each other.

When a drug is contained in the projections 22 and 32, the composition of drug contained in the forming material of the outer projection 22 and the composition of drug contained in the forming material of the inner projection 32 are varied from each other, that is, the material for forming the outer projection 22 and the material for forming the inner projection 32 are varied from each other so that different kinds of drugs are held by the projections 22 and 32. Further, when a drug is applied on the surfaces of the projections 22 and 32, the composition of drug applied on the outer projection 22 and the composition of drug applied on the inner projection 32 are varied from each other so that different kinds of drugs are held by the projections 22 and 32. Moreover, one of the outer projection 22 and the inner projection 32 may be configured to contain a drug in the projection, and the other may be configured to hold a drug on the surface of the projection. In this case, compositions on these drugs may be different from each other.

As a configuration in which the kind of drug held by the outer projection 22 and the kind of drug held by the inner projection 32 are different from each other, the following configuration is specifically preferred. That is, the outer projection 22 is made of a material of a mixture of a water soluble material and a drug or made of a water soluble material which serves as a drug. In this configuration, the outer projection 22 contains a drug therein. The inner projection 32 is also made of a material of a mixture of a water soluble material and a drug or made of a water soluble material which serves as a drug. In this configuration, the inner projection 32 contains a drug therein. Here, the composition of the drug contained in the outer projection 22 and the composition of the drug contained in the inner projection 32 are different from each other. As a result, the transdermal administration device 10 easily enables a plurality of functions as the administration functions of the projections.

The drug held by the outer projection 22 and the drug held by the inner projection 32 are not specifically limited as long as they have different compositions, and are appropriately selected depending on the purposes.

For example, when the drug held by the outer projection 22 and the drug held by the inner projection 32 are different in the time required from administration to onset of the drug or the duration over which the drug remains effective, the transdermal administration device 10 can perform effective drug administration.

Moreover, the drug held by the outer projection 22 and the drug held by the inner projection 32 may be drugs that are not easily mixed, or may be drugs that are dissolved in different solvents and are not easily dissolved in the material solution of the projections. In this configuration, drugs that have been difficult to administer together by a single transdermal administration device in the prior technique can be administered together by the transdermal administration device 10.

Moreover, one of the drug held by the outer projection 22 and the drug held by the inner projection 32 may be a drug that assists the function of the other of the drugs. In this configuration as well, the transdermal administration device 10 can perform effective drug administration. For example, the drug held by the outer projection 22 may be a drug that promotes the effectiveness of the drug held by the inner projection 32. Alternatively, the drug held by the outer projection 22 may be a drug containing a dye. In this case, when the drug held by the outer projection 22 and the drug held by the inner projection 32 are administered, the skin is colored by the drug held by the outer projection 22 so that the position where the drug held by the inner projection 32 has been administered is indicated as a position surrounded by the colored portion. As a result, the position where the drug held by the inner projection 32 has been administered can be easily located. Accordingly, if the drug needs to be administered at different positions each time of administration, the position where the drug has been previously administered can be easily located.

The administration function of the outer projection 22 and the administration function of the inner projection 32 are also different in how the holes are formed during puncture by the projections and how the drug is administered depending on how the holes are formed. Accordingly, the shape of the outer projection 22 and the shape of the inner projection 32 are different from each other, and thus the shape of the hole formed by the outer projection 22 and the shape of the hole formed by the inner projection 32 are different from each other. Further, how the holes are formed and how the drug is administered can also be varied by having different rigidity between the outer projection 22 and the inner projection 32.

For example, in the configuration having the length H1 of the outer projection 22 and the length H2 of the inner projection 32 which are different from each other, the depth of the hole formed by the outer projection 22 and the depth of the hole formed by the inner projection 32 are different from each other. As a result, the administration position of the drug held by the outer projection 22 and the administration position of the drug held by the inner projection 32 are different from each other. For example, when the length H1 of the outer projection 22 is longer than the length H2 of the inner projection 32, the drug held by the outer projection 22 is administered to a position deeper than the drug held by the inner projection 32 is administered. Specifically, the drug held by the inner projection 32 can be retained in the epidermis, while the drug held by the outer projection 22 is delivered into the dermis. In this configuration as well, the transdermal administration device 10 can perform effective drug administration.

Moreover, in the configuration in which the outer projection 22 and the inner projection 32 have different shapes and thus different volumes and different surface areas, the volumes and surface areas of the holes formed by the projections 22 and 32 are also different from each other. Therefore, the dose that can be administered by a single outer projection 22 and the dose that can be administered by a single inner projection 32 are different from each other. As a result, by virtue of the difference in the way of administration of drug, the dose administered by a single outer projection 22 and the dose administered by a single inner projection 32 can be varied with ease.

The administration function of the outer projection 22 and the administration function of the inner projection 32 are also different in the rate of drug diffusion into the body of administration target. The rate of drug diffusion can be varied by using different materials for forming the outer projection 22 and the inner projection 32.

For example, when the projections 22 and 32 are made of a water soluble material, water soluble materials having different solubility in water are used for the water soluble material which is the main component of the outer projection 22 and the water soluble material which is the main component of the inner projection 32. Accordingly, the dissolving rate of the outer projection 22 and the dissolving rate of the inner projection 32 when the projections 22 and 32 pierce the skin are varied from each other. As a result, the diffusion rate of the drug contained in the outer projection 22 and the diffusion rate of the drug contained in the inner projection 32 can be varied from each other. Specifically, when a water soluble polymer is used as the water soluble material, the weight-average molecular weight of the water soluble polymer which is the main component of the outer projection 22 may be smaller than the weight-average molecular weight of the water soluble polymer which is the main component of the inner projection 32 to thereby enable the dissolving rate of the outer projection 22 higher than the dissolving rate of the inner projection 32.

Moreover, for the drug holding form, one of the outer projection 22 and the inner projection 32 may be made of a thermoplastic resin and hold a drug on the surface of the projection, and the other may be made of a water soluble material and hold a drug in the projection. In this configuration, the drug applied on the surface of the projection can be diffused faster than the drug contained in the projection.

Therefore, according to the configuration in which the outer projection 22 and the inner projection 32 have different rates of drug diffusion into the body, the transdermal administration device 10 can perform effective drug administration.

Further, the outer projection 22 and the inner projection 32 may have a plurality of different functions for the aforementioned administration functions. For example, the outer projection 22 and the inner projection 32 may have different kinds of drugs to be administered by the projection and may have different drug administration positions. Alternatively, the outer projection 22 and the inner projection 32 may have different kinds of drugs to be administered by the projection and may have different rates of drug diffusion into the body of administration target.

<Production Method of Transdermal Administration Device>

With reference to FIGS. 4 to 7, a production method of the above transdermal administration device will be described.

First, a production method of the inner needle 30 will be described.

Figure 4:
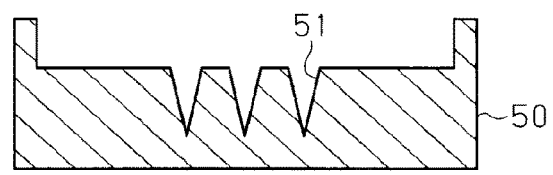
FIG. 4 is a view which illustrates a production process of the transdermal administration device of the first embodiment, and illustrates a cross section of a produced intaglio plate.

As shown in FIG. 4, an intaglio plate 50 having a recess 51 formed in conformity with the shape of the inner needle 30 is produced. In producing the intaglio plate 50, an original plate having the shape identical to the shape of the desired inner needle 30 is first produced. The shape of the original plate determines the shape of the inner needle 30 to be produced. The original plate may be produced by a known method suitable for the shape of the original plate, for example, by using a micromachining technique. The micromachining technique includes lithography, wet etching, dry etching, sand blasting, laser processing, micromachining, and the like.

Next, the intaglio plate 50 having an inverted shape of recesses and projections of the original plate is produced from the original plate. The intaglio plate 50 is produced by a known shape-transfer technique. The shape-transfer technique includes a method of producing the intaglio plate 50 made of nickel by nickel electroforming, a method of transfer molding using a molten resin, and the like.

Accordingly, the intaglio plate 50 having the recess 51 which is a recess of the shape in conformity with the inner projection 32 is produced.

Figure 5:
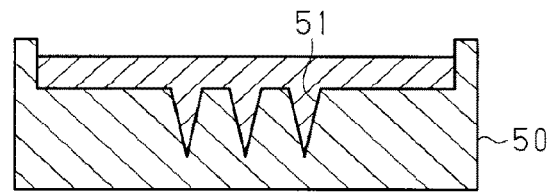
FIG. 5 is a view which illustrates a production process of the transdermal administration device of the first embodiment, and illustrates a step of filling a material into the intaglio plate.

As shown in FIG. 5, the produced recess 51 of the intaglio plate 50 is filled with a material for forming the inner needle 30.

For example, when the inner needle 30 is made of a water soluble material, a material solution containing a water soluble material and a drug is prepared. The fluidity of the material solution is preferably adjusted to an extent such that the material solution is smoothly filled into the recess 51 by adjusting the amount of the solute or the like as appropriate. The way of supplying the material solution into the recess 51 may be appropriately selected from known methods taking into consideration the shape or size of the recess 51 or the like. For example, the material solution can be supplied by methods such as spin coating, use of dispenser, casting, and ink jetting. The material solution may be supplied to the recess 51 under normal pressure, but preferably under reduced pressure or vacuum in order to smoothly supply the material solution into the recess 51. The amount of material solution supplied to the recess 51 is preferably at least such an extent that the recess having the shape in conformity with the inner projection 32 is entirely covered with the material solution.

When the material solution filled into the recess 51 is dried and solidified, a molded product which serves as the inner needle 30 is produced.

In this production method, the material solution having an increased concentration of the drug may be initially filled into the recess 51, that is, may be filled into the distal end portion of the inner projection 32 so that the drug is contained at a higher concentration in the distal end portion of the inner projection 32.

Further, when the inner needle 30 is made of a thermoplastic resin, a molded product is produced in the recess 51 by filling the thermoplastic resin into the recess 51 by thermal pressing of the sheet shaped thermoplastic resin placed on the recess 51 or by filling the thermoplastic resin into the mold including the intaglio plate 50 by injection molding.

Figure 6:
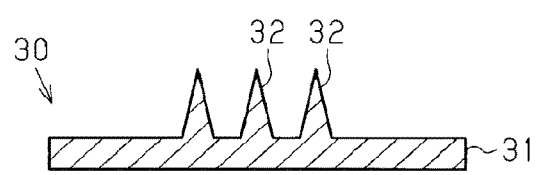
FIG. 6 is a view which illustrates a production process of the transdermal administration device of the first embodiment, and illustrates an inner needle formed by removing a molded product from the intaglio plate.

As shown in FIG. 6, the molded product in the recess 51 of the intaglio plate 50 is removed from the intaglio plate 50 to thereby obtain the microneedle 30. The molded product may be punched out by machining to shape the contour of the inner needle 30. When the inner needle 30 is made of a thermoplastic resin, a drug is applied on the surface of the inner projection 32. The drug may be applied on the surface of the inner projection 32 by known methods, for example, by using a coater or dispenser or by immersing the distal portion of the inner projection 32 into a drug solution layer which contains a drug.

The outer needle 20 is also produced in the same manner as that of the inner needle 30 depending on the forming material of the outer needle 20. The aperture 23 of the outer needle 20 may be formed by punching a center portion of the molded product by machining after the molded product is removed from the intaglio plate, or alternatively, the molded product having the aperture may be produced by filling the forming material into the intaglio plate having the inverted shape of the outer needle 20 including the aperture 23.

Figure 7:
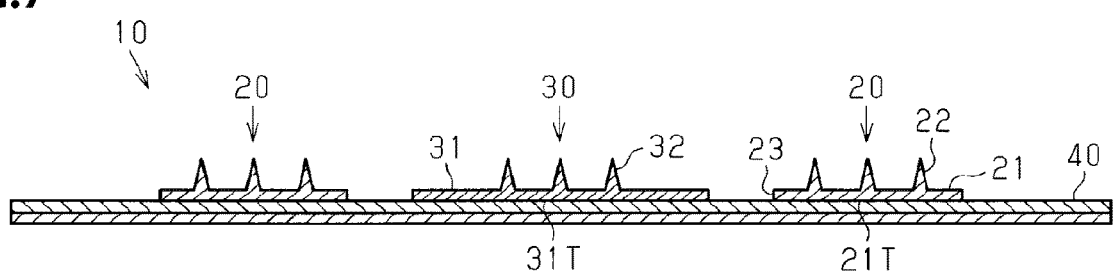
FIG. 7 is a view which illustrates a production process of the transdermal administration device of the first embodiment, and illustrates the transdermal administration device formed by adhering an adhesive sheet to an outer needle and an inner needle.

As shown in FIG. 7, the inner needle 30 is disposed inside the aperture 23 of the outer needle 20, and the adhesive sheet 40 is adhered to the first non-administration surface 21T of the outer substrate 21 and the second non-administration surface 31T of the inner substrate 31 to thereby form the transdermal administration device 10.

In use of the transdermal administration device 10, the outer substrate 21 and the inner substrate 31 are pressed against the skin with the outer projection 22 and the inner projection 32 oriented to the skin of administration target, and the adhesive sheet 40 exposed between the outer substrate 21 and the inner substrate 31 and outside the substrate 21 is affixed to the skin. As a result, the transdermal administration device 10 is fixed to the administration target with the outer projection 22 and the inner projection 32 pierced into the skin so that the drug held by the outer projection 22 and the drug held by the inner projection 32 are delivered into the body of administration target through the holes created by the projections 22 and 32.

<Effects>

Effects of the transdermal administration device 10 of the first embodiment will be described.

The transdermal administration device 10 includes two microneedles, the outer needle 20 and the inner needle 30, which are separated from each other. Accordingly, the outer needle 20 and the inner needle 30 can be independently produced. As a result, the outer projection 22 and the inner projection 32 can hold different kinds of drugs, can be formed in different shapes, or can be made of different forming materials in a simple manner.

For example, among the recesses of a single intaglio plate, it is difficult to fill part of the recesses which corresponds to a plurality of projections with a material different from others. However, in the present embodiment, the outer needle 20 and the inner needle 30 can be readily made of materials different from each other since the outer needle 20 and the inner needle 30 are independently produced. Moreover, the outer needle 20 and the inner needle 30 can be produced by production methods different from each other.

Therefore, according to the present embodiment, the transdermal administration device 10 enables a plurality of functions as the administration functions of the projections while preventing the production process of the transdermal administration device 10 from being complicated.

Specifically, the outer substrate 21 of the outer needle 20 has an annular shape, and the inner substrate 31 of the inner needle 30 is disposed inside the annulus formed by the outer substrate 21. Accordingly, the administration function of the outer projection 22 and the administration function of the inner projection 32 can be readily uniformly performed to the site where the transdermal administration device 10 is applied compared with a configuration in which the outer needle 20 and the inner needle 30 are arranged in one direction. For example, when the different kinds of drugs are administered by the outer projection 22 and the inner projection 32, the different kinds of drugs are prevented from being administered at non-uniform positions in the site where the transdermal administration device 10 is applied.

Further, since the outer needle 20 and the inner needle 30 are adhered to a single adhesive sheet 40, the two needles 20 and 30 can be collectively handled, thereby reducing a risk of the two needles 20 and 30 being separated from each other. As a result, the transdermal administration device 10 having the two needles 20 and 30 can be easily handled, allowing for easy drug administration. Moreover, since the two needles 20 and 30 can almost simultaneously pierce the skin, the drug held by the outer projection 22 and the drug held by the inner projection 32 can be simultaneously diffused into the body with ease. On the other hand, when these drugs are desired to be diffused into the body at different rates, a time difference for the diffusion can be easily designed on the basis of the time when the two needles 20 and 30 are pierced into the skin.

As described above, according to the transdermal administration device of the first embodiment, the following effects can be obtained.

(1) Since the transdermal administration device 10 includes the two needles 20 and 30 separated from each other, the needles 20 and 30 can be independently produced, thereby enabling different administration functions to be imparted to the projections 22 and 32 of the needles 20 and 30, respectively. Accordingly, the transdermal administration device 10 enables a plurality of functions as the administration functions of the projections while preventing the production process of the transdermal administration device 10 from being complicated.

In particular, since the inner substrate 31 of the inner needle 30 is disposed in a space surrounded by the outer substrate 21 of the outer needle 20, the administration function of the outer projection 22 and the administration function of the inner projection 32 can be prevented from being non-uniformly performed in the site where the transdermal administration device 10 is applied.

(2) Since the outer needle 20 and the inner needle 30 are adhered to a single adhesive sheet 40, the two needles 20 and 30 can be collectively handled, thereby allowing for easy handling of the transdermal administration device 10.

In particular, the inner substrate 31 has a shape smaller than the aperture 23 defined by the inner peripheral edge of the outer substrate 21 when viewed in the perpendicular direction. A gap is formed between the outer substrate 21 and the inner substrate 31 so as to surround the inner substrate 31, and the adhesive sheet 40 is exposed through the gap. That is, the adhesive sheet 40 is exposed outside the outer substrate 21 and between the outer substrate 21 and the inner substrate 31. Accordingly, when the transdermal administration device 10 is affixed to the skin of administration target, the transdermal administration device 10 can be fixed to the skin in a stable manner.

(3) In the configuration in which the kind of drug held by the outer projection 22 and the kind of drug held by the inner projection 32 are different from each other, different kinds of drugs can be administered by the projections 22 and 32 due to difference between the administration function of the outer projection 22 and the administration function of the inner projection 32. Accordingly, the transdermal administration device 10 can perform effective drug administration.

In particular, in the configuration in which a drug is contained in the projection, it is quite difficult to produce a microneedle configured such that part of the projections contains a composition of drug different from that of the other projections among the plurality of projections in a single microneedle by partially varying the forming materials of the projections. Therefore, a significant advantage is provided by applying the configuration having two separated needles 20 and 30 to the above drug holding form.

(4) In the configuration in which the shape of the outer projection 22 and the shape of the inner projection 32 are different from each other, the way the holes are formed during puncture by the projections 22 and 32 and the way the drugs are administered into the holes formed can be varied due to difference between the administration functions of the outer projection 22 and the administration functions of the inner projection 32. Accordingly, the transdermal administration device 10 can perform effective drug administration.

(5) In the configuration in which the forming material of the outer projection 22 and the forming material of the inner projection 32 are different from each other, different kinds of drugs can be administered by the projections 22 and 32 or the drugs can be diffused in the body of administration target at different rates due to difference between the administration function of the outer projection 22 and the administration function of the inner projection 32. Accordingly, the transdermal administration device 10 can perform effective drug administration.

Second Embodiment

Figure 8:
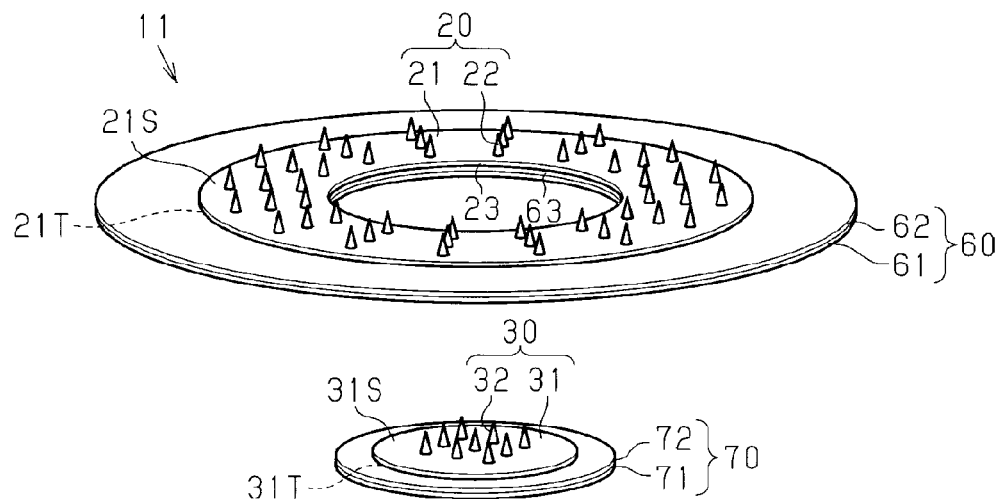
FIG. 8 is a perspective view which illustrates a perspective structure of the transdermal administration device of a second embodiment.
Figure 9:
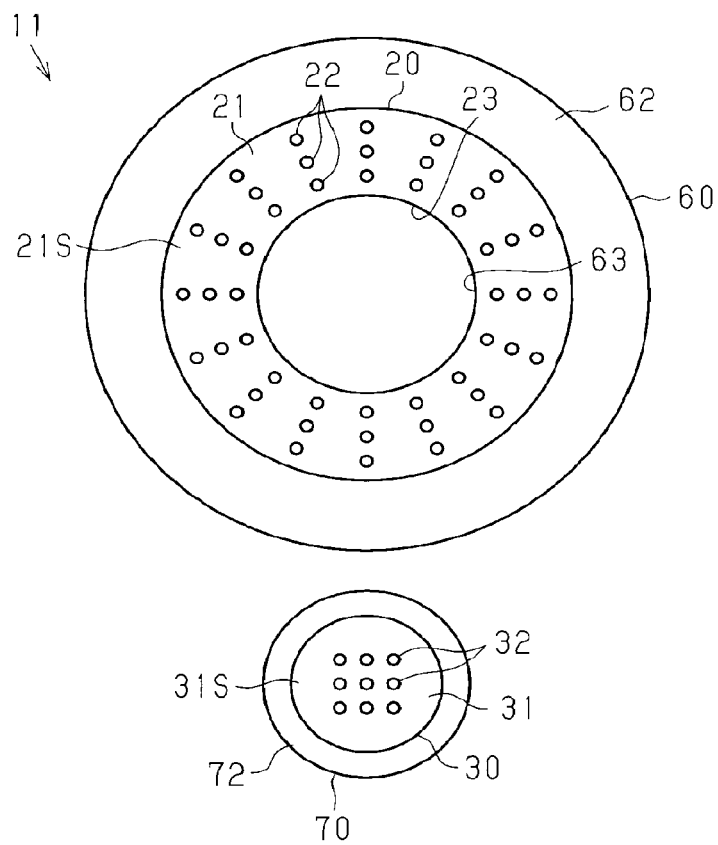
FIG. 9 is a plan view which shows a plan structure of the transdermal administration device of the second embodiment.

With reference to FIGS. 8 and 9, a second embodiment of the transdermal administration device will be described. The second embodiment differs from the first embodiment in that the transdermal administration device includes two separated adhesive sheets. The following will be described focusing on the difference from the first embodiment, and the configuration same as that of the first embodiment is referred to by the same reference numbers and the description thereof will be omitted.

<Configuration of Transdermal Administration Device>

With reference to FIGS. 8 and 9, an overall configuration of a transdermal administration device will be described.

As shown in FIG. 8, a transdermal administration device 11 includes the outer needle 20 and the inner needle 30 having the same configuration as that of the first embodiment, an outer adhesive sheet 60 which is an example of a first adhesive sheet, and an inner adhesive sheet 70 which is an example of a second adhesive sheet.

The outer adhesive sheet 60 includes an outer base sheet 61 and an outer adhesive layer 62 which covers one of two surfaces of the outer base sheet 61. The outer adhesive layer 62 is adhered to the first non-administration surface 21T of the outer substrate 21 of the outer needle 20. The outer adhesive sheet 60 has an annular shape as viewed in the first direction which is perpendicular to the first administration surface 21S, and the inner peripheral edge of the outer substrate 21 and the inner peripheral edge of the outer adhesive sheet 60 are overlapped. That is, an aperture 63 having the same outer shape as that of the aperture 23 is defined by the inner peripheral edge of the outer adhesive sheet 60.

The inner adhesive sheet 70 includes an inner base sheet 71 and an inner adhesive layer 72 which covers one of two surfaces of the inner base sheet 71. The inner adhesive layer 72 is adhered to the second non-administration surface 31T of the inner substrate 31 of the inner needle 30. When viewed in the second direction which is perpendicular to the second administration surface 31S, the inner adhesive sheet 70 has a circular shape and has a size that can be disposed inside the apertures 23 and 63.

As shown in FIG. 9, the outer shape of the outer adhesive sheet 60 is larger than the outer substrate 21 when viewed in the first direction. That is, the outer adhesive sheet 60 extends outward from the outer substrate 21 and the outer adhesive layer 62 is exposed when viewed in the first direction. The outer shape of the outer adhesive sheet 60 is not specifically limited as long as it is an annular shape, and the adhesive sheet 60 has, for example, a circular annular shape when viewed in the first direction.

The outer shape of the inner adhesive sheet 70 is larger than the inner substrate 31 when viewed in the second direction. That is, the inner adhesive sheet 70 extends outward from the inner substrate 31 and the inner adhesive layer 72 is exposed when viewed in the second direction.

The outer shape of the inner adhesive sheet 70 as viewed in the second direction is preferably smaller than the outer shape of the apertures 23 and 63 as viewed in the first direction. The outer shape of the inner adhesive sheet 70 as viewed in the second direction preferably has a shape that can be disposed in a single space surrounded by the outer adhesive sheet 60 when viewed in the first direction, and may have a circular shape smaller than the apertures 23 and 63 or may have a shape other than a circular shape.

The outer adhesive sheet 60 and the inner adhesive sheet 70 preferably have the identical thickness. When the inner needle 30 is disposed inside the apertures 23 and 63 of the outer needle 20, the inner adhesive sheet 70 is preferably disposed inside the aperture 63 of the outer adhesive sheet 60 and the inner substrate 31 is preferably disposed inside the aperture 23 of the outer substrate 21.

<Production Method of Transdermal Administration Device>

In the transdermal administration device 11 of the second embodiment, the outer needle 20 and the inner needle 30 are produced in the same manner as that of the first embodiment. After that, the outer adhesive sheet 60 having the aperture 63 is adhered to the first non-administration surface 21T of the outer substrate 21 of the outer needle 20, and the inner adhesive sheet 70 is adhered to the second non-administration surface 31T of the inner substrate 31 of the inner needle 30 to thereby form the transdermal administration device 11.

In use of the transdermal administration device 11, the substrate 21 is first pressed against the skin with the outer projection 22 of the outer needle 20 oriented to the skin of administration target, and the outer adhesive sheet 60 which is exposed outside the outer substrate 21 is affixed to the skin. Then, the inner substrate 31 is pressed against the skin with the inner projection 32 of the inner needle 30 oriented to the skin exposed from the apertures 23 and 63 of the outer needle 20, and the inner adhesive sheet 70 which is exposed outside the inner substrate 31 is affixed to the skin.

In short, the outer needle 20 is fixed to the skin of administration target, and then the inner needle 30 is fixed to the skin inside the apertures 23 and 63 of the outer needle 20. As a result, the transdermal administration device 11 is fixed to the administration target with the outer projection 22 and the inner projection 32 pierced into the skin so that the drug held by the outer projection 22 and the drug held by the inner projection 32 are delivered into the body of administration target through the holes created by the projections 22 and 32.

Alternatively, the outer needle 20 may be fixed at a position surrounding the inner needle 30 after the inner needle 30 is fixed to the skin.

In the second embodiment, it is preferred that the drug held by the outer projection 22 is the drug initially introduced into the skin, and the drug held by the inner projection 32 is the drug introduced into the skin subsequent to the drug held by the outer projection 22. In use of the transdermal administration device 11 having such a configuration, the outer needle 20 is fixed to the skin of administration target and then the inner needle 30 is fixed to the skin inside the apertures 23 and 63 of the outer needle 20. For a user of the transdermal administration device 11, it is easy to first fix the outer needle 20 to the skin and then fix the inner needle 30 to the skin compared with first fixing the inner needle 30 to the skin and then fixing the outer needle 20 to the skin. Therefore, according to the above configuration, the drug administration consistent with the order of administration can be easily performed.

<Effects>

Effects of the transdermal administration device 11 of the second embodiment will be described.

In a similar manner to the first embodiment, the transdermal administration device 11 of the second embodiment includes the outer needle 20 and the inner needle 30 which are separated from each other. Accordingly, the outer needle 20 and the inner needle 30 can be independently produced. In this configuration, different administration functions can be imparted to the projections 22 and 32 of the needles 20 and 30, and therefore, the transdermal administration device 11 enables a plurality of functions as the administration functions of the projections while preventing the production process of the transdermal administration device 11 from being complicated.

In use of the transdermal administration device 11, since the inner needle 30 can be disposed inside the annulus formed by the outer needle 20, the administration function of the outer projection 22 and the administration function of the inner projection 32 can be readily uniformly performed to a site where the transdermal administration device 11 is applied.

In the transdermal administration device 11 of the second embodiment, since the outer adhesive sheet 60 adhered to the outer needle 20 and the inner adhesive sheet 70 adhered to the inner needle 30 are separated from each other, the outer needle 20 and the inner needle 30 can be individually handled. As a result, drug administration by the outer needle 20 and drug administration by the inner needle 30 can be performed with a time difference.

Further, since the inner adhesive sheet 70 has a shape that can be disposed inside the annulus formed by the outer adhesive sheet 60, the outer adhesive sheet 60 and the inner adhesive sheet 70 are prevented from overlapping with each other when the outer needle 20 and the inner needle 30 are applied to the skin. This prevents a decrease in percentage of the area to be affixed to the skin in the adhesive sheets 60 and 70. As a result, the adhesive surfaces of the adhesive sheets 60 and 70 can be effectively used to affix the outer needle 20 and the inner needle 30 to the skin.

As described above, according to the transdermal administration device of the second embodiment, the following effects can be obtained in addition to the effects (1), (3) to (5) of the first embodiment.

(6) Since the outer adhesive sheet 60 adhered to the outer needle 20 and the inner adhesive sheet 70 adhered to the inner needle 30 are separated from each other, the outer needle 20 and the inner needle 30 can be individually handled. In addition, the inner adhesive sheet 70 has a shape that can be disposed in the space surrounded by the outer adhesive sheet 60. Accordingly, the adhesive surfaces of the adhesive sheets 60 and 70 can be effectively used to affix the outer needle 20 and the inner needle 30 to the skin.

In particular, in the configuration in which the inner adhesive sheet 70 has a shape smaller than the aperture 63 defined by the inner peripheral edge of the outer adhesive sheet 60 as viewed in the first direction when the inner needle 30 is viewed in the second direction, the two needles 20 and 30 can be easily affixed to the skin of an administration target in sequence.

Modified Examples

The above embodiments can be implemented with modifications as described below.

In the first and second embodiments, the outer shape of the outer substrate 21 of the outer needle 20 is only required to be an annular shape when viewed in the first direction, and may also be an annular rectangular shape or an annular ellipse shape. Further, the outer shape of the inner substrate 31 of the inner needle 30 as viewed in the second direction may also be a rectangular shape or an ellipse shape as long as it can be disposed inside the space surrounded by the outer substrate 21 as viewed in the first direction.

Figure 10:
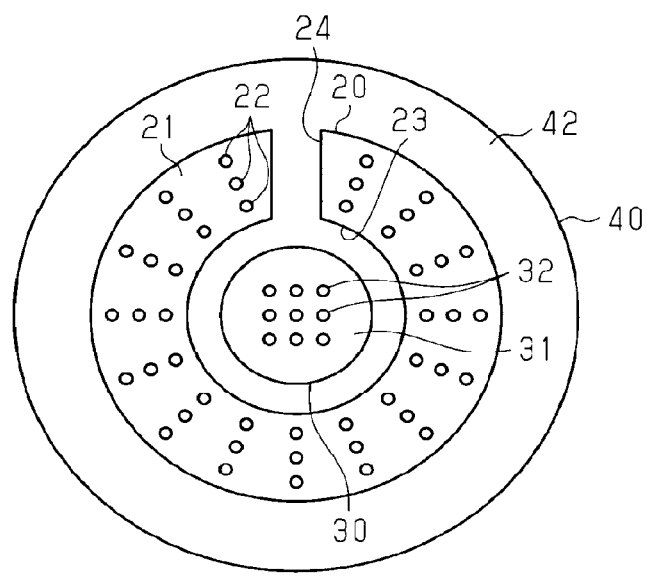
FIG. 10 is a plan view which shows a plan structure of the transdermal administration device of a modified example.
Figure 11:
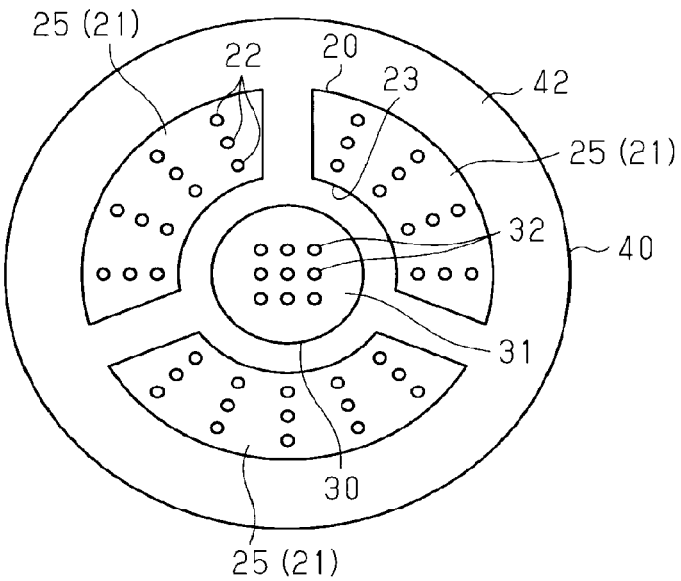
FIG. 11 is a plan view which shows a plan structure of the transdermal administration device of a modified example.

Moreover, the outer substrate 21 of the outer needle 20 is only required to be disposed on an annulus that surrounds a space as viewed in the first direction, and the outer substrate 21 may not be necessarily formed as a closed annular shape. For example, as shown in FIG. 10, the outer substrate 21 may include a gap 24 in a portion in the circumferential direction. The gap 24 extends along the entire outer substrate 21 in the radial direction of the outer substrate 21. Alternatively, as shown in FIG. 11, the outer substrate 21 may be made up of a plurality of substrate pieces 25 that are disposed on an annulus with intervals therebetween. In the example shown in FIG. 11, the outer substrate 21 is made up of three arc-shaped substrate pieces 25. In this configuration as well, the effect similar to the above (1) can be obtained if the inner substrate 31 can be disposed in the space surrounded by a virtual annulus formed by connecting the ends of the outer substrate 21 to each other.

Figure 12:
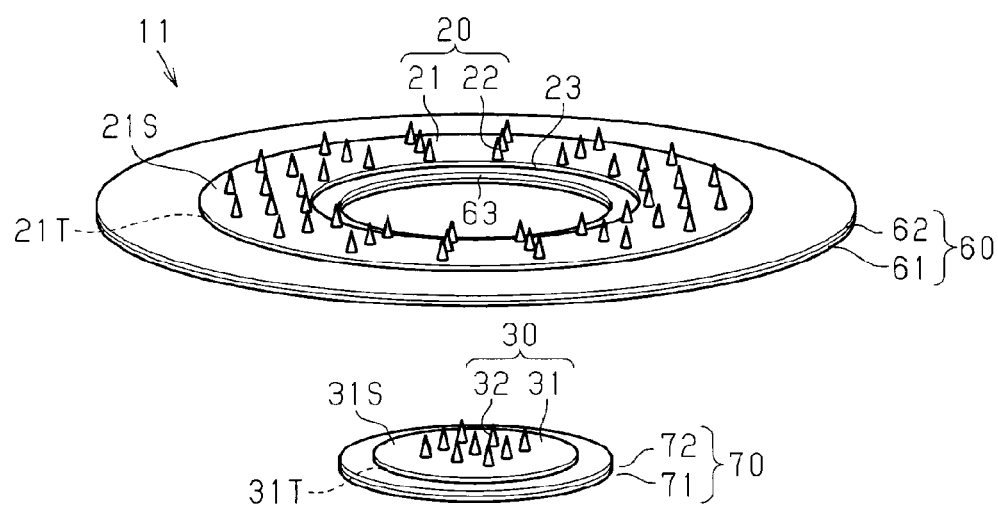
FIG. 12 is a perspective view which shows a perspective structure of the transdermal administration device of a modified example.

In the second embodiment, as shown in FIGS. 8 and 9, the outer shape of the aperture 23 of the outer needle 20 is consistent with the outer shape of the aperture 63 of the outer adhesive sheet 60 as viewed in the first direction. Instead of that configuration, as shown in FIG. 12, the aperture 63 of the outer adhesive sheet 60 may be smaller than the aperture 23 of the outer needle 20. That is, the outer adhesive sheet 60 may extend inward from the aperture 23 of the outer needle 20 when viewed in the first direction.

In the second embodiment, the outer adhesive sheet 60 and the inner adhesive sheet 70 may partially overlap each other when the outer needle 20 and the inner needle 30 are applied to the skin. For example, if the outer shape of the inner substrate 31 is smaller than the apertures 23 and 63, the outer shape of the inner adhesive sheet 70 may be larger than the apertures 23 and 63, or the inner peripheral edge of the outer adhesive sheet 60 may be located inside the inner peripheral edge of the outer substrate 21 as viewed in the first direction. Further, when in use, if the inner needle 30 is fixed to the skin prior to fixing the outer needle 20, and the outer needle 20 is applied on the skin outside the area where the inner needle 30 is fixed, the outer adhesive sheet 60 does not necessarily have the aperture 63.

In the above embodiments, the drug holding form of the projections 22 and 32 includes a configuration of the projections 22 and 32 having a drug held on the surfaces of the projections 22 and 32 and a configuration of the projections 22 and 32 having a drug contained in the projections 22 and 32, but the drug holding form is not limited thereto. For example, the projections 22 and 32 may have a groove or hole, and a drug in the form of powder or liquid may be filled in the groove or hole. In the configuration in which the drug holding form of the outer projection 22 and the drug holding form of the inner projection 32 are different from each other, the rate of drug diffusion into the body of administration target may differ between the outer projection 22 and the inner projection 32.

Alternatively, at least one of the outer projection 22 and the inner projection 32 may have a through hole that penetrates the projections 22 and 32 and the substrates 21 and 31 so that a drug is introduced from the outside into the skin via the through hole by using a syringe or the like. In this configuration, the projections 22 and 32 do not necessarily hold the drug until they are pierced into the skin. Further, an adhesive sheet may not be necessarily adhered to a portion of the first non-administration surface 21T of the outer substrate 21 and the second non-administration surface 31T of the inner substrate 31 in which the through hole is formed. For example, in the transdermal administration device, the outer projection 22 may hold a drug on the surface and the inner projection 32 may have a through hole, and the adhesive sheet 40 may be adhered to the first non-administration surface 21T of the outer substrate 21 and an outer peripheral portion of the second non-administration surface 31T of the inner substrate 31. In use of the transdermal administration device having the above configuration, the drug on the surface of the outer projection 22 is delivered into the skin and a drug is introduced from the outside into the skin via the through hole of the inner projection 32 when the transdermal administration device is fixed to the skin.

The shape of the projection of the administration member is not limited to a needle shape, that is, the shape extending in a direction perpendicular to the administration surface of the substrate. The shape of the projection may be a blade shape, that is, a linear shape in which the projection extends in an extending direction along the administration surface of the substrate and a distal portion of the projection extends not in the direction perpendicular to the administration surface of the substrate but in a direction, for example, extending along the extending direction. For example, the projection may be formed as a triangular prism shape that extends along the extending direction while one of three rectangular side surfaces of the triangular prism is in contact with the substrate and the side of the triangular prism that partitions the other two side surfaces serves as a tip of the projection.

At least one of the outer needle 20 and the inner needle 30 may have a multi-layered structure. For example, in the outer needle 20, the outer projection 22 may include a plurality of portions made of different materials in the extending direction, or the outer projection 22 and the outer substrate 21 may be made of different materials, or the outer substrate 21 may include a plurality of portions made of different materials in the thickness direction. Similarly, in the inner needle 30, the inner projection 32 may include a plurality of portions made of different materials in the extending direction, or the inner projection 32 and the inner substrate 31 may be made of different materials, or the inner substrate 31 may include a plurality of portions made of different materials in the thickness direction. According to this configuration, when the outer needle 20 and the inner needle 30 are made of a water soluble material, a drug may be held only by the projections 22 and 32 or only by the distal portion of the projections 22 and 32.

The transdermal administration device may include three or more administration members. When the substrate of the second administration member has a shape that can be disposed in a space surrounded by the annulus formed by the substrate of the first administration member, a substrate of a third administration member may be arranged side by side with the substrate of the second administration member in the above space. Alternatively, the substrate of the second administration member may be disposed on an annulus smaller than the above annulus and the substrate of the third administration member may be disposed in a space surrounded by the annulus formed by the second administration member.

EXAMPLES

The aforementioned transdermal administration device will be described by using specific examples.

Example 1

<Production of Intaglio Plate>

An original plate of the inner needle was formed from a silicon substrate by micromachining. Thirty six inner projections were arrayed on an inner substrate in a 6×6 matrix with a pitch of 1 mm, and each inner projection was formed in a regular quadrangular pyramid shape (height: 150 μm, bottom: 60 μm×60 μm).

An original plate of the outer needle was formed from a silicon substrate by micromachining. The original plate included a center circular region of 15 mmφ in which a projection is not provided. The shape and arrangement pitch of the outer projections were the same as those of the inner projections.

Then, the original plate for the inner needle was plated with nickel to a thickness of 500 μm. Then, the original plate for the inner needle made of silicon was wet-etched with potassium hydroxide solution of weight percent concentration of 30% which was heated at a temperature of 90° C. to produce an intaglio plate made of nickel. An intaglio plate for the outer needle was produced from an original plate for the outer needle in the same manner as that of the inner needle.

<Preparation of Material Solution>

A hydroxypropyl cellulose aqueous solution with a weight percent concentration of 5% was prepared by dissolving hydroxypropyl cellulose in water. Then, rhodamine B was added as a drug to the hydroxypropyl cellulose aqueous solution to prepare a material solution for the inner needle. Further, Evans Blue was added as a drug to the hydroxypropyl cellulose aqueous solution to prepare a material solution for the outer needle.

<Fabrication of Inner Needle>

The intaglio plate for the inner needle was filled with the material solution for the inner needle, and heated by using a hot plate heated to 90° C. to thereby dry and solidify the material solution. The solidified molded product was removed from the intaglio plate. Then, the molded product was punched into a circle of 12 mmφ to thereby obtain the inner needle.

<Fabrication of Outer Needle>

The intaglio plate for the outer needle was filled with the material solution for the outer needle, and heated by using a hot plate heated to 90° C. to thereby dry and solidify the material solution. The solidified molded product was removed from the intaglio plate. Then, the center circular region of the molded product was punched out to thereby obtain the outer needle.

<Production of Transdermal Administration Device>

The inner needle was disposed inside the center aperture of the obtained outer needle. The adhesive sheet was adhered to the outer needle and the inner needle to thereby obtain the transdermal administration device of Example 1.

Example 2

<Production of Intaglio Plate>

An original plate for the inner needle and an original plate for the outer needle which includes a center aperture of 15 mmϕ were produced in the same manner as Example 1. An intaglio plate for the inner needle and an intaglio plate for the outer needle were produced from these original plates. The intaglio plate of the outer needle included a center aperture of 15 mmϕ.

<Fabrication of Inner Needle and Outer Needle>

The intaglio plate for the inner needle was filled with a polyethylene resin by thermal pressing, and the molded product was removed from the intaglio plate to thereby obtain the inner needle. Similarly, the intaglio plate for the outer needle was filled with a polyethylene resin by thermal pressing, and the molded product was removed from the intaglio plate to thereby obtain the outer needle. A guide was provided in thermal pressing so that the inner needle and the outer needle were fabricated without a punching process. Then, drugs are individually applied on the inner projections of the inner needle and the outer projections of the outer needle.

<Production of Transdermal Administration Device>

The inner needle was disposed inside the center aperture of the obtained outer needle. The adhesive sheet was adhered to the outer needle and the inner needle to thereby obtain the transdermal administration device of Example 2.

Example 3

<Fabrication of Inner Needle and Outer Needle>

The inner needle was fabricated in the same manner as Example 2. Further, the outer needle was fabricated in the same manner as Example 1.

<Production of Transdermal Administration Device>

The inner needle was disposed inside the center aperture of the obtained outer needle. The adhesive sheet was adhered to the outer needle and the inner needle to thereby obtain the transdermal administration device of Example 3.

Example 4

<Fabrication of Inner Needle and Outer Needle>

Further, the inner needle and the outer needle were fabricated in the same manner as Example 1.

<Fabrication of Outer Adhesive Sheet>

An adhesive sheet of a circular annular shape having an aperture of 15 mmϕ at a center of the sheet was provided as an outer adhesive sheet.

<Fabrication of Inner Adhesive Sheet>

An adhesive sheet of a circular shape of 15 mmϕ was provided as an inner adhesive sheet.

<Production of Transdermal Administration Device>

The outer needle was adhered to the outer adhesive sheet, aligning the center aperture of the outer needle with the center aperture of the outer adhesive sheet. The inner needle was adhered to the inner adhesive sheet, aligning the center of the circular inner substrate of the inner needle with the center of the circular inner adhesive sheet. Thus, the transdermal administration device of Example 4 was obtained.

As described above, microneedles include projections which are micro-structures and collectively disposed on each substrate in each microneedle. These projections may be formed at the same time by filling the material into the mold. As a consequence, it has been difficult to divide these projections into a plurality of groups having different drug administration functions.

Specifically, it has been difficult to vary the kinds of drugs administered by different groups, for example, by varying the drugs applied on the projections or by varying the drugs contained in the forming material of the projections. Further, it has also been difficult to vary how the holes are formed by different groups during puncture by the projections by varying the shape of the mold of the projections to vary the shape of the projections. Therefore, it is desirable to develop transdermal administration devices that can administer a plurality of kinds of drugs simultaneously, for example, by imparting different administration functions to different groups of projections.

An embodiment of the present invention is a transdermal administration device that enables a plurality of functions as the drug administration functions of the projections.

A transdermal administration device includes a first administration member which includes a first substrate having a first administration surface and a first non-administration surface which is a surface opposite from the first administration surface, and a first projection protruding from the first administration surface, the first projection having a first administration function. The transdermal administration device further includes a second administration member which includes a second substrate having a second administration surface and a second non-administration surface which is a surface opposite from the second administration surface, and a second projection protruding from the second administration surface, the second projection having a second administration function. The first substrate is disposed on an annulus that surrounds a space when the first administration member is viewed in a first direction which is a direction perpendicular to the first administration surface, and the second substrate has a shape that is disposed in the space as viewed in the first direction when the second administration member is viewed in a second direction which is a direction perpendicular to the second administration.

According to the above configuration, the first administration member and the second administration member are separated from each other in the transdermal administration device. Accordingly, these administration members can be independently produced, and different administration functions can be imparted to the projections of each of the administration members. Therefore, the transdermal administration device enables a plurality of functions as the administration functions of the projections.

Further, since the second substrate is disposed in the space surrounded by the first substrate when the transdermal administration device is used for drug administration, the administration function of the first projection and the administration function of the second projection can be prevented from being non-uniformly performed in the site where the transdermal administration device is applied.

The above transdermal administration device may further include an adhesive sheet adhered to the first non-administration surface and the second non-administration surface. In this configuration, it is preferred that the adhesive sheet extends outward from the first substrate when viewed in a direction perpendicular to the first administration surface and the second administration surface.

According to the above configuration, since the first administration member and the second administration member are adhered to a single adhesive sheet, the two administration members can be collectively handled, thereby allowing for easy handling of the transdermal administration device.

In the above transdermal administration device, the first substrate may have an annular shape, and the second substrate may have a shape smaller than an aperture defined by an inner peripheral edge of the first substrate, and a gap may be formed between the first substrate and the second substrate so as to surround the second substrate, and the adhesive sheet may be exposed through the gap when viewed in a direction perpendicular to the first administration surface and the second administration surface.

According to the above configuration, the adhesive sheet is exposed between the first substrate and the second substrate in addition to outside the first substrate. Accordingly, when the transdermal administration device is affixed to the skin of administration target, the transdermal administration device can be fixed to the skin in a stable manner.

The transdermal administration device may further include a first adhesive sheet adhered to the first non-administration surface, and a second adhesive sheet adhered to the second non-administration surface. In this configuration, it is preferred that the first adhesive sheet has an annular shape that surrounds a space, and the first adhesive sheet extends outward from the first substrate when the first administration member is viewed in the first direction, and the second adhesive sheet has a shape that is disposed in the space surrounded by the first adhesive sheet as viewed in the first direction, and the second adhesive sheet extends outward from the second substrate when the second administration member is viewed in the second direction.

According to the above configuration, since the first adhesive sheet adhered to the first administration member and the second adhesive sheet adhered to the second administration member are separated from each other, the first administration member and the second administration member can be independently handled. Further, since the second adhesive sheet has a shape that can be disposed inside the space surrounded by the first adhesive sheet, the two adhesive sheets are prevented from overlapping with each other when the first administration member and the second administration member are applied to the skin. Accordingly, the adhesive surfaces of the adhesive sheets can be effectively used to affix the first administration member and the second administration member to the skin.

In the above transdermal administration device, the second adhesive sheet may have a shape smaller than an aperture defined by an inner peripheral edge of the first adhesive sheet as viewed in the first direction when the second administration member is viewed in the second direction.

According to the above configuration, the two administration members, that is, the first administration member and the second administration member can be easily affixed to the skin of an administration target in sequence.

In the above transdermal administration device, the first projection and the second projection may each hold a drug, and a kind of drug held by the first projection and a kind of drug held by the second projection may be different from each other.

According to the above configuration, a kind of drug administered by the first projection and a kind of drug administered by the second projection are different from each other, and functions of administering different kinds of drugs can be achieved as the first administration function of the first projection and the second administration function of the second projection. As a result, the transdermal administration device can perform effective drug administration.

In the above transdermal administration device, the first projection may include a drug in the first projection, and the second projection may include a drug in the second projection, and a composition of the drug contained in the first projection and a composition of the drug contained in the second projection may be different from each other.

According to the above configuration, a kind of drug administered by the first projection and a kind of drug administered by the second projection are different from each other, and functions of administering different kinds of drugs can be achieved as the first administration function of the first projection and the second administration function of the second projection. In particular, in the configuration in which a drug is contained in the projection, it is quite difficult to produce an administration member configured such that part of the projections contains a composition of drug different from that of the other projections among the plurality of projections in a single administration member by partially varying the forming materials of the projections. Therefore, a significant advantage is provided by using the configuration in which the first administration member and the second administration member are separated from each other.

In the above transdermal administration device, a shape of the first projection and a shape of the second projection may be different from each other.

According to the above configuration, the way how the holes are formed by the projections and the way how the drugs are administered into the holes formed are different between the first projection and the second projection as the first administration function and the second administration function. Accordingly, the drug administration functions of each of the projections enable functions different from each other, and the transdermal administration device can perform effective drug administration.

In the above transdermal administration device, a material constituting the first projection and a material constituting the second projection may be different from each other.

According to the above configuration, the first administration function of the first projection and the second administration function of the second projection enable a function of administering different kinds of drugs or a function of diffusing a drug into the body of administration target at different rates. As a result, the transdermal administration device can perform effective drug administration.

The transdermal administration device enables a plurality of functions as the administration functions of the projections.

REFERENCE SIGNS LIST 10, 11 . . . transdermal administration device
20 . . . outer needle
21 . . . outer substrate
21S . . . first administration surface
21T . . . first non-administration surface
22 . . . outer projection
23 . . . aperture
30 . . . inner needle 31 ... inner substrate
31S ... second administration surface
31T ... second non-administration surface
32 ... inner projection
40 ... adhesive sheet
41 ... base sheet
42 ... adhesive layer
50 ... intaglio plate
51 ... recess
60 ... outer adhesive sheet
61 ... outer base sheet
62 ... outer adhesive layer
63 ... aperture
70 ... inner adhesive sheet
71 ... inner base sheet
72 ... inner adhesive layer Obviously, numerous modifications and variations of the present invention are possible in light of the above teachings. It is therefore to be understood that within the scope of the appended claims, the invention may be practiced otherwise than as specifically described herein.

What is claimed is:

1. A transdermal administration device, comprising:
an adhesive sheet comprising a first adhesive sheet portion and a second adhesive sheet portion;
a first administration member adhered on a surface of the first adhesive sheet portion and comprising a first substrate and a plurality of first projections protruding from a first administration surface of the first substrate; and
a second administration member adhered on a surface of the second adhesive sheet portion and comprising a second substrate and a plurality of second projections protruding from a second administration surface of the second substrate,
wherein the adhesive sheet is formed such that the first adhesive sheet portion is an outer adhesive sheet having an annular shape with an opening and that the second adhesive sheet portion is an inner adhesive sheet positioned inside the opening of the outer adhesive sheet and separates from the first adhesive sheet portion, the first administration member has an aperture, and the second substrate is positioned on the surface of the second adhesive sheet portion such that the second administration member is positioned within the aperture of the first administration member, the plurality of second projections in the second administration member is arrayed in a rectangular matrix, and the plurality of first projections in the first administration member is arrayed radially.

2. The transdermal administration device of claim 1, wherein the adhesive sheet is larger than the first administration member such that the adhesive sheet extends outward from the first substrate when viewed in a direction perpendicular to the first administration surface.

3. The transdermal administration device of claim 2, wherein the first substrate has an annular shape having the aperture defined by an inner peripheral edge of the first substrate, and the second substrate is positioned within the aperture with a gap formed between the first substrate and the second substrate such that the adhesive sheet is exposed through the gap when viewed in a direction perpendicular to the first administration surface and the second administration surface.

4. The transdermal administration device of claim 1, wherein the adhesive sheet is formed such that the first adhesive sheet portion is larger than the first administration member and extends outward from the first substrate, and that the second adhesive sheet portion is larger than the second administration member and not larger than the opening.

5. The transdermal administration device of claim 4, wherein the second adhesive sheet portion is smaller than the opening defined by an inner peripheral edge of the first adhesive sheet portion when viewed in the direction perpendicular to the second administration surface.

6. The transdermal administration device of claim 1, wherein the plurality of first projections and the plurality of second projections comprise drug formulations such that the drug formulation in the first projections includes an active ingredient different from an active ingredient of the drug formulation in the second projections.

7. The transdermal administration device of claim 3, wherein the plurality of first projections and the plurality of second projections comprise drug formulations such that the drug formulation in the first projections includes an active ingredient different from an active ingredient of the drug formulation in the second projections.

8. The transdermal administration device of claim 5, wherein the plurality of first projections and the plurality of second projections comprise drug formulations such that the drug formulation in the first projections includes an active ingredient different from an active ingredient of the drug formulation in the second projections.

9. The transdermal administration device of claim 1, wherein the plurality of first projections and the plurality of second projections comprise drug formulations such that the drug formulation in the first projections has a composition different from a composition of the drug formulation in the second projections.

10. The transdermal administration device of claim 3, wherein the plurality of first projections and the plurality of second projections comprise drug formulations such that the drug formulation in the first projections has a composition different from a composition of the drug formulation in the second projections.

11. The transdermal administration device of claim 5, wherein the plurality of first projections and the plurality of second projections comprise drug formulations such that the drug formulation in the first projections has a composition different from a composition of the drug formulation in the second projections.

12. The transdermal administration device of claim 1, wherein the first projections have a shape that is different from a shape of the second projections.

13. The transdermal administration device of claim 3, wherein the first projections have a shape that is different from a shape of the second projections.

14. The transdermal administration device of claim 5, wherein the first projections have a shape that is different from a shape of the second projections.

15. The transdermal administration device of claim 1, wherein the plurality of first projections comprises a material that is different from a material of the plurality of second projections.

16. The transdermal administration device of claim 3, wherein the plurality of first projections comprises a material that is different from a material of the plurality of second projections.

17. The transdermal administration device of claim 5, wherein the plurality of first projections comprises a material that is different from a material of the plurality of second projections.

18. The transdermal administration device of claim 1, wherein the adhesive sheet is formed such that a thickness of the first adhesive sheet portion is equal to a thickness of the second adhesive sheet portion.

19. The transdermal administration device of claim 4, wherein the second administration member has a gap formed in the second substrate such that the gap extends radially and connected to the gap formed between the first substrate and the second substrate.

20. The transdermal administration device of claim 1, wherein the second substrate of the second administration member comprises a plurality of substrate pieces positioned in an annular form with an interval.

* * * * *